United States Patent
Ikku

(10) Patent No.: US 9,349,572 B2
(45) Date of Patent: May 24, 2016

(54) ENERGY DISPERSIVE X-RAY ANALYZER AND METHOD FOR ENERGY DISPERSIVE X-RAY ANALYSIS

(71) Applicant: Hitachi High-Tech Science Corporation, Minato-ku, Tokyo (JP)

(72) Inventor: Yutaka Ikku, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 0 days.

(21) Appl. No.: 14/664,423

(22) Filed: Mar. 20, 2015

(65) Prior Publication Data

US 2015/0270094 A1     Sep. 24, 2015

(30) Foreign Application Priority Data

Mar. 20, 2014    (JP) ................................. 2014-058389

(51) Int. Cl.
*H01J 37/26*      (2006.01)
*H01J 37/28*      (2006.01)

(52) U.S. Cl.
CPC ...................................... *H01J 37/28* (2013.01)

(58) Field of Classification Search
USPC ................. 250/305, 306, 307, 309, 310, 311, 250/492.1, 492.3
See application file for complete search history.

(56) References Cited

U.S. PATENT DOCUMENTS

| | | | | |
|---|---|---|---|---|
| 6,493,082 B2 * | 12/2002 | Nara et al. | ..................... | 356/394 |
| 2013/0054153 A1 * | 2/2013 | Motl et al. | ..................... | 702/28 |
| 2013/0240728 A1 * | 9/2013 | Albiol et al. | .................. | 250/305 |

FOREIGN PATENT DOCUMENTS

| | | |
|---|---|---|
| JP | H05-26826 A | 2/1993 |
| JP | 2000-214108 A | 8/2000 |

* cited by examiner

*Primary Examiner* — Nicole Ippolito
(74) *Attorney, Agent, or Firm* — Banner & Witcoff, Ltd.

(57) ABSTRACT

An energy dispersive X-ray analyzer is attached to a scanning electron microscope and includes: a SEM controller; a detector; an EDS controller; and a data processor. The data processor generates first and second X-ray mapping image respectively when the SEM controller controls the scanning electron microscope to irradiate the sample with an electron beam under first and second acceleration voltage conditions. The data processor corrects the first X-ray mapping image and the second X-ray mapping image into images that are independent of acceleration voltage condition based on a measurement intensity variation ratio of the X-ray when changed from the first acceleration voltage condition to the second acceleration voltage condition, and controls the display unit to display a difference image between the corrected first X-ray mapping image and the corrected second X-ray mapping image.

5 Claims, 2 Drawing Sheets

ENERGY DISPERSIVE X-RAY ANALYZER AND METHOD FOR ENERGY DISPERSIVE X-RAY ANALYSIS

CROSS-REFERENCE TO RELATED APPLICATION

This application claims priority from Japanese Patent Application No. 2014-058389, filed on Mar. 20, 2014, the entire subject matter of which is incorporated herein by reference.

BACKGROUND

1. Technical Field

The present invention relates to an energy dispersive X-ray analyzer that is used being attached to a scanning electron microscope and a method for energy dispersive X-ray analysis.

2. Description of the Related Art

In energy dispersive X-ray analyzers to be attached to a scanning electron microscope, X-rays that are generated by irradiating a sample with an accelerated electron beam are acquired by the energy dispersive X-ray analyzer and used for quantitative/qualitative analysis of a minute portion of the sample. For another example, a two-dimensional X-ray intensity image is obtained together with a scanning electron microscope image by scanning a sample two-dimensionally with an accelerated electron beam and acquiring generated X-rays being synchronized with the scanning.

Conventionally, for example, JP-A-2000-214108 discloses an area analysis method for a sample having an arbitrary shape that employs an electron probe microanalyzer (EPMA). A sample embedded body is used in which a sample is embedded in an embedding material. An area analysis is performed on a sample having an arbitrary shape by executing a step of setting an analysis target region in a sample embedded body and dividing the analysis target region into plural small divisional regions, a step of setting (selecting) small divisional regions each containing part of the sample, and a step of measuring and analyzing the thus-set small divisional regions successively and connecting analysis results of the respective small divisional regions.

JP-A-H05(1993)-026826 discloses a method for performing a quantitative analysis and a film thickness measurement by an X-ray spectroscopic method using an EPMA or the like in a case that a substrate and a thin film of a thin-film sample contain the same element and the constituent elements of the substrate and the thin film are known. This analyzing method is a thickness measuring method using a standard sample and is performed in the following manner. A ratio (X-ray intensity ratio) between an intensity of characteristic X-rays of a component element that are radiated from a thin-film sample (whose constituent elements are known) excited by an electron beam accelerated at a proper acceleration voltage and an intensity of X-rays radiated from a simple substance sample of the component element excited by an accelerated electron beam of the same kind is measured actually in advance (the component element should be such as to enable such an actual measurement). An X-ray intensity ratio of an element whose X-ray intensity ratio cannot be measured by an actual measurement is determined from the above-measured X-ray intensity ratio of the other element and a chemical bonding form of the measurement-incapable element and the other element. A thickness of the thin-film sample is calculated from X-ray intensity ratios of all component elements according to a particular formula, and concentrations of the respective component elements are calculated from ratios between the X-ray intensity ratios.

The above described conventional technique may have the following problems to be solved. That is, whereas the above-described techniques enable recognition of a planar element distribution by observing a two-dimensional X-ray intensity image, they do not allow users to determine an element distribution in the depth direction.

The technique disclosed in JP-A-H05(1993)-026826 relates to a thickness measurement using a standard sample and does not allow users to determine an element distribution in the depth direction.

A method for determining whether or not an element is distributed uniformly in the thickness direction is available in which a cross section of a sample is formed and an element distribution in the depth direction is recognized by performing a measurement on the cross section. However, observation of a cross section of a region of attention requires a dedicated facility and an element distribution in the depth direction can be determined only after doing long-time work of forming a cross section. As such, this method may have a problem that it takes much time and labor.

SUMMARY

The present invention has been made in view of the above-described circumstances, and one of objects of the present invention is to provide an energy dispersive X-ray analyzer which is used being attached to a scanning electron microscope and enables to determine, easily in a nondestructive manner, whether or not a measurement target element is distributed uniformly in the thickness direction, as well as a method for energy dispersive X-ray analysis using such an energy dispersive X-ray analyzer.

According to an exemplary embodiment of the present invention, there is provided an energy dispersive X-ray analyzer attached to a scanning electron microscope. The energy dispersive X-ray analyzer is provided with: a SEM controller configured to control electron beam scanning of a sample by the scanning electron microscope; a detector configured to detect X-rays generated from the sample by being irradiated with an electron beam; an EDS controller configured to process electrical signal pulses that are output from the detector; and a data processor configured to generate an X-ray mapping image based on processed electrical signal pulses and to control a display unit to display the generated X-ray mapping image. The data processor generates a first X-ray mapping image when the SEM controller controls the scanning electron microscope to irradiate the sample with an electron beam under a first acceleration voltage condition. The data processor generates a second X-ray mapping image when the SEM controller controls the scanning electron microscope to irradiate the sample with an electron beam under a second acceleration voltage condition that is different from the first acceleration voltage condition. The data processor is configured to correct the first X-ray mapping image and the second X-ray mapping image into images that are independent of acceleration voltage condition based on a measurement intensity variation ratio of the X-ray when changed from the first acceleration voltage condition to the second acceleration voltage condition, the measurement intensity variation ratio being obtained from different excitation efficiency values of generated X-rays under the first acceleration voltage condition and the second acceleration voltage condition. The data processor is configured to control the display unit to display a difference image between the corrected first X-ray mapping image and the corrected second X-ray mapping image.

According to another exemplary embodiment of the present invention, there is provided a method for energy dispersive X-ray analysis using an energy dispersive X-ray analyzer attached to a scanning electron microscope. The energy dispersive X-ray analyzer is provided with: a SEM controller configured to control electron beam scanning of a sample by the scanning electron microscope; a detector configured to detect X-rays generated from the sample by being irradiated with an electron beam; an EDS controller configured to processes electrical signal pulses that are output from the detector; and a data processor configured to generate an X-ray mapping image based on processed electrical signal pulses and to control a display unit to display the generated X-ray mapping image. The method includes: generating a first X-ray mapping image by the data processor when the SEM controller controls the scanning electron microscope to irradiate the sample with an electron beam under a first acceleration voltage condition, generating a second X-ray mapping image by the data processor when the SEM controller controls the scanning electron microscope to irradiate the sample with an electron beam under a second acceleration voltage condition that is different from the first acceleration voltage condition; correcting, by the data processor, the first X-ray mapping image and the second X-ray mapping image into images that are independent of acceleration voltage condition based on a measurement intensity variation ratio of the X-ray when changed from the first acceleration voltage condition to the second acceleration voltage condition, the measurement intensity variation ratio being obtained from different excitation efficiency values of generated X-rays under the first acceleration voltage condition and the second acceleration voltage condition; and controlling, by the data processor, the display unit to display a difference image between the corrected first X-ray mapping image and the corrected second X-ray mapping image.

BRIEF DESCRIPTION OF THE DRAWINGS

The above and other aspects of the present invention will become more apparent and more readily appreciated from the following description of illustrative embodiments of the present invention taken in conjunction with the attached drawings, in which.

DETAILED DESCRIPTION

An energy dispersive X-ray analyzer and a method for energy dispersive X-ray analysis according to an embodiment of the present invention will be hereinafter described with reference to FIGS. 1-4.

Figure 1:
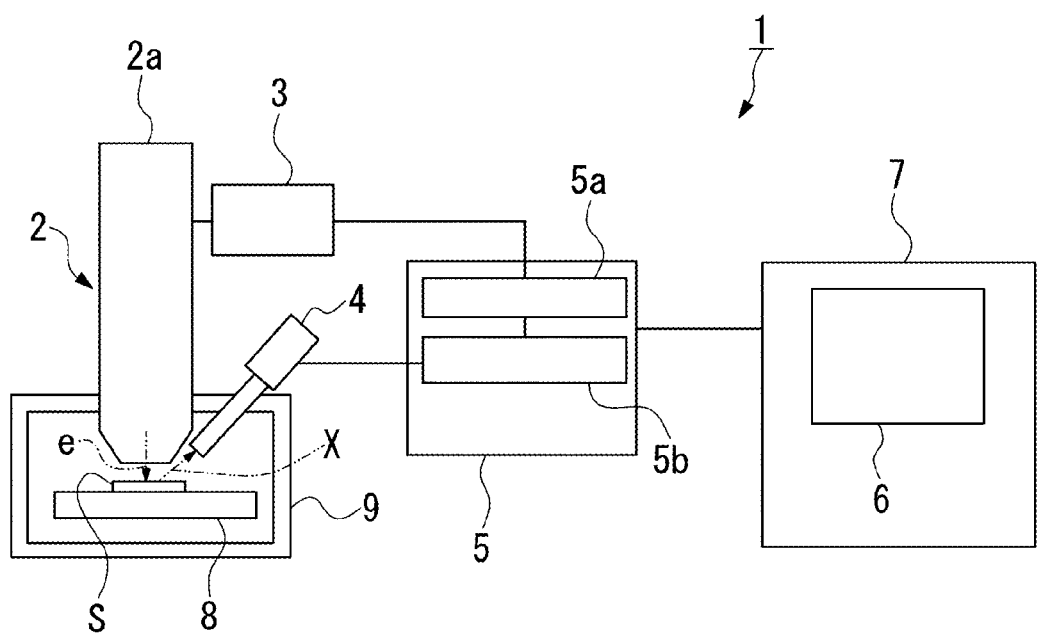
FIG. 1 is a schematic diagram showing the overall configuration of a system including an energy dispersive X-ray analyzer according to an embodiment of the invention and a scanning electron microscope.

As shown in FIG. 1, the energy dispersive X-ray analyzer 1 according to the embodiment is an energy dispersive X-ray analyzer that is attached to a scanning electron microscope 2. The energy dispersive X-ray analyzer 1 is equipped with a SEM controller 3 for controlling electron beam scanning of a sample S by the scanning electron microscope 2, a detector 4 for detecting X-rays X that are generated from the sample S being irradiated with the electron beam e, an EDS controller 5 for processing electrical signal pulses that are output from the detector 4, and a data processor 7 for generating an X-ray mapping image based on the electrical signal pulses processed and displaying it on a display unit 6.

The data processor 7 has a function of generating a first X-ray mapping image M1 (see FIG. 2) as the SEM controller 3 controls the scanning electron microscope 2 to irradiate the sample S with an electron beam e under a first acceleration voltage condition.

The data processor 7 also has a function of generating a second X-ray mapping image M2 (see FIG. 2) as the SEM controller 3 controls the scanning electron microscope 2 to irradiate the sample S with an electron beam e under a second acceleration voltage condition that is different from the first one.

For example, when the sample S is silicon (Si), the depth of its X-ray generation region is 0.3 μm under a first acceleration voltage condition of 5 kV and increases to 1.0 μm under a second acceleration voltage condition of 10 kV. As the acceleration voltage is set higher, the electron beam e goes deeper into the Si sample and X-rays are generated according to the irradiation depth.

Figure 2:
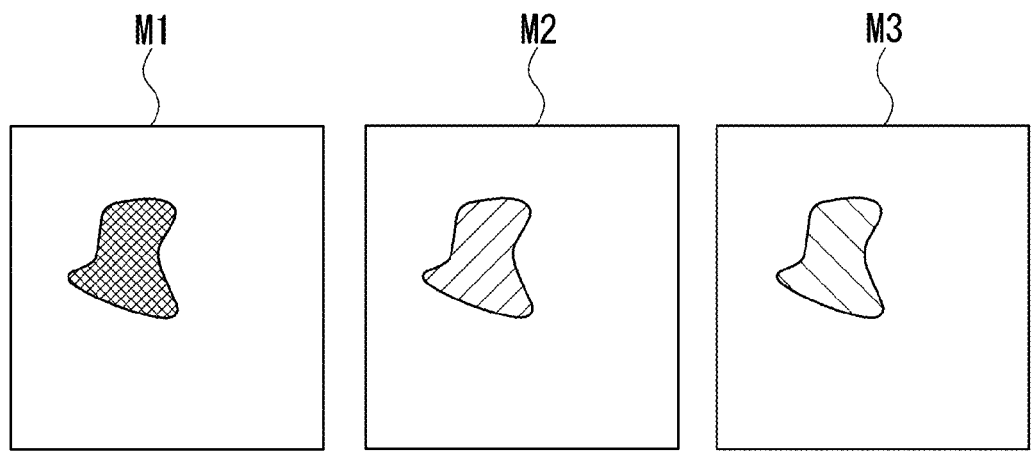
FIG. 2 shows an example difference image between a first X-ray mapping image and a second X-ray mapping image that is displayed on a display unit in the embodiment.

The data processor 7 also has a function of correcting the first X-ray mapping image M1 and the second X-ray mapping image M2 into images that are independent of the acceleration voltage condition according to an X-ray measurement intensity variation ratio of the change from the first acceleration voltage condition to the second one resulting from different excitation efficiency values of generated X-rays corresponding to the first and second acceleration voltage conditions, respectively, and displaying, on the display unit 6, a difference image M3 between the corrected first X-ray mapping image M1 and second X-ray mapping image M2 (see FIG. 2).

Figure 3:
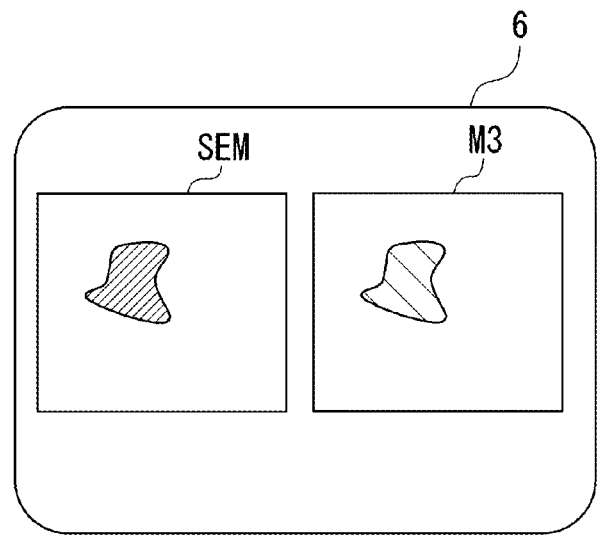
FIG. 3 shows an example scanning electron microscope image and difference image that are displayed on the display unit in the embodiment.

As shown in FIG. 3, the data processor 7 displays a scanning electron microscope image SEM acquired by the scanning electron microscope 2 on the display unit 6 together with the difference image M3 simultaneously.

Furthermore, the data processor 7 has a function of performing the above-described image correction according to a measurement intensity variation ratio that is calculated based on a first X-ray mapping image M1 and a second X-ray mapping image M2 obtained in advance from a region where an element distribution in the depth direction is uniform.

Figure 4:
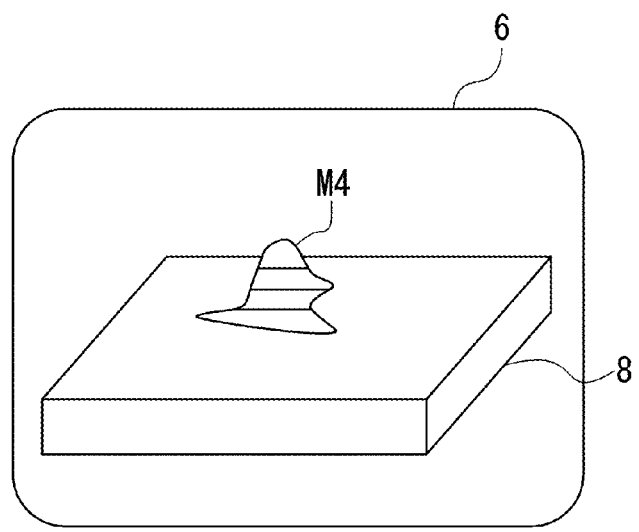
FIG. 4 shows an example distribution image that is displayed on the display unit stereographically in the embodiment.

As shown in FIG. 4, the EDS controller 5 can display, on the display unit 6, as a three-dimensional area graph, a distribution image M4 corresponding to the difference image M3 by showing corrected X-ray intensities in different colors indicating respective intensity ranges and showing corrected difference values in the form of projections and recesses.

The scanning electron microscope 2 is equipped with a SEM barrel 2a for accelerating an electron beam e and irradiating the sample S with the electron beam e, a sample stage 8 on which the sample S is placed, and a sample chamber 9 which houses the sample stage 8.

The detector 4 detects X-rays X generated from the sample S when it is irradiated with an electron beam e and generates resulting electrical signal pulses. More specifically, an X-ray incidence window of the detector 4 is provided with a semiconductor detecting device (e.g., pin diode (Si device); not shown). When receiving a single X-ray photon, the detector 4 generates a current pulse (electrical signal pulse) corresponding to it. An instantaneous current value of this current pulse is proportional to the energy of the incident characteristic X-ray. The detector 4 is set so as to convert the current pulse generated by the semiconductor detecting device into a voltage pulse, amplifies it, and outputs an amplified voltage pulse as a signal.

The EDS controller 5 is equipped with a scanning signal processor 5a and a signal processor 5b. The scan signal processor 5a generates a scanning signal to be used for the scanning electron microscope 2 to perform a scan with an electron beam e and sends it to the SEM controller 3, to generate an X-ray mapping image. The scanning signal processor 5a receives, from the detector 4, an electrical signal pulse sequence generated by detection of X-rays and generates a histogram as an X-ray energy spectrum based on heights of the electrical signal pulses. That is, the signal processor 5b is an analyzer for analyzing signals received from the detector 4 and is a multichannel pulse height analyzer which obtains voltage pulse heights from signals received from the detector 4 and thereby generates an energy spectrum.

The scanning signal processor 5a sends a scanning signal to the SEM controller 3, whereby the SEM barrel 2a scans the sample S with an electron beam e and a scanning electron microscope image SEM is displayed on the display unit 6 (see FIG. 3).

The scanning signal processor 5a sends a clock pulse to the signal processor 5b for each one-pixel scan amount, whereby X-ray measurement data corresponding to each pixel is stored in the signal processor 5b. Finally, data of an X-ray mapping image is produced. Usually, because of a limited memory capacity of the signal processor 5b, the signal processor 5b holds X-ray measurement data of one line and sends it to the data processor 7. The data processor 7 accumulates, as X-ray mapping image data, data sent from the signal processor 5b successively and displays an X-ray mapping image on the display unit 6.

The signal processor 5b has a function of receiving a clock pulse from the scanning signal processor 5a, storing X-ray measurement data of one pixel, and starting to acquire X-ray measurement data of the next pixel, to generate an X-ray mapping image. The signal processor 5b generates an X-ray measurement data sequence by repeating the above operation, whereby an X-ray mapping image is produced.

Connected to the EDS controller 5, the data processor 7 can display, on the display unit 6, a scanning electron microscope image SEM, an X-ray spectrum, a result of a quantitative analysis on an X-ray spectrum, X-ray mapping images M1 and M2 (mentioned above), a difference image M3, etc. The data processor 7 is a computer configured by electrical components such as a CPU.

Next, an analyzing method according to the embodiment that uses the energy dispersive X-ray analyzer 1 will be described.

The an analyzing method according to the embodiment has a step that the SEM controller 3 controls the scanning electron microscope 2 to irradiate a sample S with an electron beam e under a first acceleration voltage condition and the data processor 7 generates a first X-ray mapping image Ml; a step that the SEM controller 3 controls the scanning electron microscope 2 to irradiate a sample S with an electron beam e under a second acceleration voltage condition that is different from the first one and the data processor 7 generates a second X-ray mapping image M2; and a step that the data processor 7 corrects the first X-ray mapping image M1 and the second X-ray mapping image M2 into images that are independent of the acceleration voltage condition according to an X-ray measurement intensity variation ratio of the change from the first acceleration voltage condition to the second one resulting from different excitation efficiency values of generated X-rays corresponding to the first and second acceleration voltage conditions, and displays, on the display unit 6, a difference image M3 between a corrected first X-ray mapping image M1 and second X-ray mapping image M2.

The step of generating a difference image M3 will be described below in more detail. When a first X-ray mapping image M1 and a second X-ray mapping image M2 have been obtained under the first acceleration voltage condition and the second acceleration voltage condition, respectively, the data processor 7 generates a difference image M3 in one of the following three modes:

(1) Mode in which a Difference Image M3 is Obtained by Performing a Quantitative Calculation at Each Point First, the following calculations are performed for each point of X-ray mapping images. Symbols Ia(n) and Ib(n) represent measurement intensities of an element n measured at a first acceleration voltage a and a second acceleration voltage b of an electron beam e, respectively.

A concentration ratio is determined by performing a quantitative calculation using an X-ray spectrum obtained at the first acceleration voltage a.

Then a measurement intensity variation ratio k(n) of a change from the first acceleration voltage a to the second acceleration voltage b is calculated theoretically using the determined concentration ratio.

If the element n is distributed uniformly in the depth direction, the following Equation (1) should be satisfied for the measurement intensity variation ratio k(n):

$$k(n)=Ib(n)/Ia(n) \qquad (1)$$

If the element n is not distributed uniformly but has a high concentration (in terms of weight) in the vicinity of the surface, the following Equation (2) should be satisfied:

$$Ia(n)>Ib(n)/k(n) \qquad (2)$$

If the element n is distributed so as to have a high concentration (in terms of weight) in a deep region, the following Equation (3) should be satisfied:

$$Ia(n)<Ib(n)/k(n) \qquad (3)$$

Therefore, the corrected difference value Diff(n) which is defined by the following Equation (4) can be used as an index indicating whether or not the element n is distributed uniformly in the depth direction.

$$\text{Diff}(n)=Ia(n)-Ib(n)/k(n) \qquad (4)$$

Corrected difference values Diff(n) are calculated for all pixels of the generated X-ray mapping images, whereby a difference image M3 of the element n is obtained.

The above series of steps is executed for every target element.

(2) Mode in which a Difference Image M3 is Obtained by Determining Voltage Dependence of the Measurement Intensity for Each Element Using a Standard Sample First, preparatory work is done in the following manner. A standard sample is placed the sample stage 8, an X-ray measurement is performed by irradiating the standard sample with an electron beam e at a first acceleration voltage a, and a resulting X-ray spectrum XSPECa is stored. Then, an X-ray measurement is performed by irradiating the standard sample with an electron beam e at a second acceleration voltage b, and a resulting X-ray spectrum XSPECb is stored.

Although in this example measurements are performed in the two conditions, that is, at the first acceleration voltage a and the second acceleration voltage b, performing X-ray spectrum measurements additionally at other acceleration voltages in the preparatory work increases the level of completeness of preparation and hence can lower the probability of occurrence of insufficient preparation for measurement of a true sample.

Next, a difference image M3 is calculated by the data processor 7 in the following manner.

The following calculations are performed at each point of X-ray mapping images. A measurement intensity SIa(n), measured at the first acceleration voltage a, of an element n in the standard sample is calculated from the X-ray spectrum XSPECa. And a measurement intensity SIb(n), measured at the second acceleration voltage b, of the element n in the standard sample is calculated from the X-ray spectrum XSPECb.

A measurement intensity variation ratio k(n) of a change of the acceleration voltage of an electron beam e is calculated according to the following Equation (5):

$$k(n)=SIb(n)/SIa(n) \quad (5)$$

Let Ia(n) and Ib(n) represent measurement intensities of the element n measured at the first acceleration voltage a and the second acceleration voltage b, respectively. A corrected difference value Diff(n) is calculated according to the following Equation (6):

$$\mathrm{Diff}(n)=Ia(n)-Ib(n)/k(n) \quad (6)$$

Corrected difference values Diff(n) are calculated for all pixels of the generated X-ray mapping images, whereby a difference image M3 of the element n is obtained.

The above series of steps is executed for every target element.

(3) Mode in which a Difference Image M3 is Obtained by Designating a Uniform Distribution Region This is a method in which the above-described image correction is performed according to a measurement intensity variation ratio that is calculated using a first X-ray mapping image M1 and a second X-ray mapping image M2 that were obtained in advance for a region where an element distribution in the depth direction is uniform.

First, a region where the distribution of an element n in the depth direction is uniform is designated and a first X-ray mapping image M1 and a second X-ray mapping image M2 are generated for the designated region.

Region integration intensities RIa(n) and RIb(n) of the element n are calculated for the designated region from the first X-ray mapping image M1 and the second X-ray mapping image M2.

A measurement intensity variation ratio k(n) of a change of the acceleration voltage of an electron beam e is calculated by the following Equation (7):

$$k(n)=RIb(n)/RIa(n) \quad (7)$$

Let Ia(n) and Ib(n) represent measurement intensities of the element n measured at the first acceleration voltage a and the second acceleration voltage b, respectively. For each point of the X-ray mapping images M1 and M2, a corrected difference value Diff(n) is calculated according to the following Equation (8):

$$\mathrm{Diff}(n)=Ia(n)-Ib(n)/k(n) \quad (8)$$

Corrected difference values Diff(n) are calculated for all pixels of the acquired X-ray mapping images, whereby a difference image M3 of the element n is obtained.

The above series of steps is executed for every target element.

In the embodiment, as shown in FIG. 4, the EDS controller 5 displays, on the display unit 6, as a three-dimensional area graph, a distribution image M4 corresponding to a difference image M3 by showing corrected X-ray intensities (hereinafter referred to as absolute X-ray intensities) in different colors indicating respective intensity ranges and showing corrected difference values in the form of projections and recesses. For example, a portion where the absolute X-ray intensity is high is shown in red and a portion where the absolute X-ray intensity is low is shown in blue. The distribution image M4 is an area graph presenting a three-dimensional (3D) effect (i.e., 3D area graph) that has a depth dimension and in which corrected difference values are shown stereographically in the form of projections and recesses in the height direction (Z axis).

Not only is a distribution image M4 displayed that corresponds to a difference image M3 and in which corrected difference values are shown in the form of projections and recesses, but also data in which corrected difference values of an element n are selected to form projections and recesses may be displayed in the form of a 3D area graph against a scanning electron microscope image SEM. Furthermore, data in which measurement values of a first X-ray mapping image M1 of an element n are selected to form projections and recesses may be displayed in the form of a 3D area graph against a scanning electron microscope image SEM.

As described above, in the energy dispersive X-ray analyzer 1 according to the embodiment, the data processor 7 corrects a first X-ray mapping image M1 and a second X-ray mapping image M2 into images that are independent of the acceleration voltage condition according to an X-ray measurement intensity variation ratio of a change from a first acceleration voltage condition to a second one resulting from different excitation efficiency values of generated X-rays corresponding to the first and second acceleration voltage conditions, respectively, and displays, on the display unit 6, a difference image M3 between the corrected first X-ray mapping image M1 and second X-ray mapping image M2. Thus, an element distribution in the depth direction is detected in the form of the difference image M3.

More specifically, if two corrected X-ray intensity distribution images obtained under different acceleration voltage conditions (i.e., a corrected first X-ray mapping image M1 and second X-ray mapping image M2) have approximately equal numerical values, a difference image M3 has corrected difference values that are close to zero and it is determined that the element is distributed uniformly in the depth direction. On the other hand, if a difference image M3 has corrected difference values that are certain non-zero values, it can be determined from the sign of the corrected difference values whether the element is mainly distributed near the surface or in a low layer.

Measurements can be performed as long as the acceleration voltage is higher than or equal to a minimum acceleration voltage that enables excitation of characteristic X-rays to be measured. Therefore, where it is desired to determine in a thin layer whether or not an element is distributed uniformly in the thickness direction, two electron beam acceleration voltages are employed that are relatively close to the minimum acceleration voltage. Where it is desired to determine in a thick layer whether or not an element is distributed uniformly in the thickness direction, two electron beam acceleration voltages having a large difference are employed. In this manner, the electron beam acceleration voltages are selected according to the thickness in which to determine whether or not an element is distributed uniformly.

The data processor 7 can display a scanning electron microscope image SEM obtained by the scanning electron microscope 2 on the display unit 6 together with a difference image M3 simultaneously. Displaying a difference image M3 and a scanning electron microscope image SEM such as a secondary electron image simultaneously makes it possible to recognize differences between them visually.

Furthermore, the data processor 7 performs the above-described image correction according to a measurement intensity variation ratio that is calculated from a first X-ray mapping image M1 and a second X-ray mapping image M2 that were obtained in advance for a region where the element distribution in the thickness direction is uniform. This makes it unnecessary to produce a correction value database using samples whose compositions are known and to determine a correction value by a quantitative analyzing method and sample current correction. Therefore, where it is known that a measurement sample has a region where the element distribution in the thickness direction is uniform, determining a correction value (measurement intensity variation ratio) by designating this region as a region of attention makes it possible to generate a corrected first X-ray mapping image M1 and second X-ray mapping image M2 easily. Thus, increase in practicality is attained.

For example, by setting, as such a region of attention, a thick $SiO_2$ region of a semiconductor device or the like, the analyzing method according to the embodiment can be applied to a determination for a thin $SiO_2$ region.

Still further, the EDS controller 5 can display, on the display unit 6, as a three-dimensional area graph, a distribution image corresponding to a difference image M3 by showing corrected X-ray intensities in different colors indicating respective intensity ranges and showing corrected difference values in the form of projections and recesses. This makes it possible to determine a corrected X-ray intensity distribution and an element distribution in the thickness direction with a high level of visual recognition using a stereographic display method.

The technical scope of the invention is not limited to the above-described embodiment, and various modifications are possible without departing from the spirit and scope of the invention.

The present invention provides the following advantages. In the energy dispersive X-ray analyzer and the method for energy dispersive X-ray analysis according to the invention, a first X-ray mapping image and a second X-ray mapping image are corrected into images that are independent of the acceleration voltage condition according to an X-ray measurement intensity variation ratio resulting from different excitation efficiency values of generated X-rays corresponding to first and second acceleration voltage conditions, respectively, and a difference image between the corrected first X-ray mapping image and second X-ray mapping image is displayed on the display unit. As a result, an element distribution in the depth direction can be detected in the form of the difference image. Thus, the invention makes it possible to determine, easily in a nondestructive manner, whether or not a measurement target element is distributed uniformly in the thickness direction.

What is claimed is:

1. An energy dispersive X-ray analyzer attached to a scanning electron microscope, the energy dispersive X-ray analyzer comprising:

a SEM controller configured to control electron beam scanning of a sample by the scanning electron microscope;
a detector configured to detect X-rays generated from the sample by being irradiated with an electron beam;
an EDS controller configured to process electrical signal pulses that are output from the detector; and
a data processor configured to generate an X-ray mapping image based on the processed electrical signal pulses and to control a display unit to display the generated X-ray mapping image,
wherein the data processor generates a first X-ray mapping image when the SEM controller controls the scanning electron microscope to irradiate the sample with an electron beam under a first acceleration voltage condition,
wherein the data processor generates a second X-ray mapping image when the SEM controller controls the scanning electron microscope to irradiate the sample with an electron beam under a second acceleration voltage condition that is different from the first acceleration voltage condition,
wherein the data processor is configured to correct the first X-ray mapping image and the second X-ray mapping image into images that are independent of acceleration voltage conditions based on a measurement intensity variation ratio of the X-ray when changed from the first acceleration voltage condition to the second acceleration voltage condition, the measurement intensity variation ratio being obtained from different excitation efficiency values of generated X-rays under the first acceleration voltage condition and the second acceleration voltage condition, and
wherein the data processor is configured to control the display unit to display a difference image between the corrected first X-ray mapping image and the corrected second X-ray mapping image.

2. The energy dispersive X-ray analyzer according to claim 1,
wherein the data processor is configured to control the display unit to display a scanning electron microscope image obtained by the scanning electron microscope together with the difference image simultaneously.

3. The energy dispersive X-ray analyzer according to claim 1,
wherein the data processor is configured to perform the image correction based on the measurement intensity variation ratio that is calculated based on the first X-ray mapping image and the second X-ray mapping image obtained in advance for a region where an element distribution in the depth direction is uniform.

4. The energy dispersive X-ray analyzer according to claim 1,
wherein the EDS controller is configured to control the display unit to display a distribution image as a three-dimensional area graph, the distribution image corresponding t the difference image by showing corrected X-ray intensities in different colors indicating respective intensity ranges and showing corrected difference values in a form of projections and recesses.

5. A method for energy dispersive X-ray analysis using an energy dispersive X-ray analyzer attached to a scanning electron microscope,
wherein the energy dispersive X-ray analyzer comprises:
a SEM controller configured to control electron beam scanning of a sample by the scanning electron microscope;
a detector configured to detect X-rays generated from the sample by being irradiated with an electron beam;

an EDS controller configured to process electrical signal pulses that are output from the detector; and a data processor configured to generate an X-ray mapping image based on the processed electrical signal pulses and to control a display unit to display the generated X-ray mapping image, wherein the method comprises:

generating a first X-ray mapping image by the data processor when the SEM controller controls the scanning electron microscope to irradiate the sample with an electron beam under a first acceleration voltage condition;

generating a second X-ray mapping image by the data processor when the SEM controller controls the scanning electron microscope to irradiate the sample with an electron beam under a second acceleration voltage condition that is different from the first acceleration voltage condition;

correcting, by the data processor, the first X-ray mapping image and the second X-ray mapping image into images that are independent of acceleration voltage conditions based on a measurement intensity variation ratio of the X-ray when changed from the first acceleration voltage condition to the second acceleration voltage condition, the measurement intensity variation ratio being obtained from different excitation efficiency values of generated X-rays under the first acceleration voltage condition and the second acceleration voltage condition; and controlling, by the data processor, the display unit to display a difference image between the corrected first X-ray mapping image and the corrected second X-ray mapping image.

* * * * *